(12) United States Patent
Greaves et al.

(10) Patent No.: US 7,749,286 B2
(45) Date of Patent: Jul. 6, 2010

(54) COMPOSITION FOR DYEING KERATIN FIBERS AND A METHOD OF DYEING HAIR USING SAME

(75) Inventors: Erjena Greaves, New York, NY (US); Jeffrey T. Greaves, New York, NY (US)

(73) Assignee: Advanced Cosmetic Technologies, LLC, New York, NY (US)

( * ) Notice: Subject to any disclaimer, the term of this patent is extended or adjusted under 35 U.S.C. 154(b) by 0 days.

(21) Appl. No.: 12/467,725

(22) Filed: May 18, 2009

(65) Prior Publication Data

US 2009/0249563 A1    Oct. 8, 2009

Related U.S. Application Data

(63) Continuation-in-part of application No. 11/381,061, filed on May 1, 2006, now Pat. No. 7,550,014.

(51) Int. Cl.
*A61Q 5/10*    (2006.01)

(52) U.S. Cl. .................. 8/405; 8/425; 8/435; 8/628; 8/629; 8/637.1; 8/646; 8/653

(58) Field of Classification Search .............. 8/405, 8/425, 435, 628, 629, 637.1, 646, 653
See application file for complete search history.

(56) References Cited

U.S. PATENT DOCUMENTS

2002/0053110 A1 *   5/2002   Dias et al. .................. 8/405

\* cited by examiner

*Primary Examiner*—Eisa B Elhilo
(74) *Attorney, Agent, or Firm*—Wiggin and Dana LLP

(57) ABSTRACT

A composition for dyeing keratin fibers that contains 0.1 to 30 percent of at least one substantially pure plant dye material obtained using solvent or supercritical $CO_2$ extraction, combined with 0.01 to 5 percent of active metal in a metal or mineral salt capable of acting as a mordant as a two-part hair color system.

24 Claims, No Drawings

COMPOSITION FOR DYEING KERATIN FIBERS AND A METHOD OF DYEING HAIR USING SAME

CROSS-REFERENCE TO RELATED APPLICATIONS

This application is a continuation-in-part of U.S. application Ser. No. 11/381,061, filed May 1, 2006 now U.S. Pat. No. 7,550,014.

FIELD OF THE DISCLOSURE

This disclosure relates to hair dyes, specifically to the use of substantially pure plant dye substances obtained by solvent or supercritical $CO_2$ extraction, with or without metallic or mineral salts, to make intense, fast-acting, long lasting hair dyes.

BACKGROUND OF THE DISCLOSURE

Synthetic hair color formulations currently on the market typically fall into one of two categories: permanent and semi-permanent.

Permanent hair color formulations consist primarily of oxidative dye systems based on the dual action of two types of precursors—bases (primary intermediates) and modifiers (couplers). Bases are typically aromatic diamines, diaminophenols, aminophenols, while couplers are typically m-diamines, m-aminophenols and polyphenols (Charles Zviak, The Science of Hair Care, Marcel Dekker Inc., New York, 1986, pp. 265-268; Joseph Rivlin, The Dyeing of Textile Fibers, PCT&S, Philadelphia, 1992, pp. 30-52). The wash fastness of permanent dyes is about 30-40 shampoo cycles. There are, however, a number of issues with permanent dyes. The primary amine used in these oxidative dye systems is generally paraphenilene-diamine (PPD), for which there is growing evidence of and concern over its carcinogenicity and mutagenicity (The Use of Permanent Hair Dyes and Bladder Cancer Risk, SCCNFP/484/01, 2001). Other oxidative dye system precursors, such as the coupler resorcinol, also show toxicity (David Steiman & Samuel Epstein, The Safe Shopper's Bible, Macmillan, 1995, pp. 240-243). The oxidative action of these types of dye systems is provided by hydrogen peroxide at a high pH, which is known to damage hair and irritate the scalp and skin. Most patented developments in the permanent dye area are aimed at decreasing toxicity, hair damage and irritation (J. F. Corbett, Hair Coloring, Clinics in Dermatology, vol. 6, no. 3, 1988, pp. 96-101).

Semi-permanent hair color formulations are those based on the use of coal tar dyes. Coal tar dyes fall into direct, acid, and basic color index categories. The wash fastness of these dyes is about 2-10 shampoo cycles (Charles Zviak, The Science of Hair Care, Marcel Dekker Inc., New York, 1986, pp. 242-261). Recent studies in toxicology and ecology have identified most coal tar dyes, especially direct (as defined by color index) and mono-azo/di-azo (as defined by structure) dyes (the most red and red-orange shades), as carcinogens, teratogens and mutagens (David Steinman & Samuel Epstein, The Safe Shopper's Bible, Macmillan, 1995, pp. 240-243). Acid dyes in particular are known to stain the scalp and skin. Most patented technologies in this area are aimed at decreasing toxicity and irritation, as well as regulating fastness and leveling. Leveling refers to the process of spreading the color from the dye evenly over the hair.

The toxicity of current permanent and semi-permanent synthetic hair color formulations is such that many U.S. physicians do not recommend hair coloring during pregnancy, for people with cancer, or for people at high risk of cancer (David Steinman & Samuel Epstein, The Safe Shopper's Bible, Macmillan, 1995, p. 241).

The main problems with using natural dyes (as opposed to synthetic hair color formulations) to color hair have always been that natural hair dyes produce dull shades of color and have poor wash fastness to shampoo. Natural sources of dyes, such as plants, contain low concentrations of colorants, and the dyes that are recovered from those natural sources are often impure and have poor solubility (H. S. Freeman & A. T. Peters, Colorants for Non-Textile Applications, Elsevier, 2000, pp. 382-453). These problems result in products with long and inconvenient application times for natural hair color technology. Moreover, most natural hair dyes are offered in powder form, which is inconvenient for the user.

There are a number of different natural plant dyes available. Those plant dyes include, but are not limited to, Brazilwood, Logwood Extract, Hematine, Indigo, Quercetin, Madder, alizarine, rubiethyric acid, purpuroxanthin, rubiadin, morindanigrin, munjistin, morindadiol, carotene, crocetin, bixin, canthaxanthin, lycopene, capsanthin, apocarotenal, xanthophyll, curcumin, morin, malclurin, luteolin, apigenin, fakugetin, datiscetin, kaempferol, rhamnocitrin, rhamnethin, zanthorhamnin, Isorhamnetin, Rhamnazin, Rutin, Gossypetin, Butin/Butein, Rottlerin, Chlorophyll A/B, Catechin, Fisetin, Lapachol, Juglone, Alkannin, Alkannan, Deoxysantalin, Atromentin, Awobamin, Carajuirin, Dracorhodin, Berberine, Betanin, Orcein, Xanthone, Naphthalene, Riboflavin, Anthocyanin, Lawsone, emblica extract, alfalfa extract, black tea extract, green tea extract, white tea extract, and red sandalwood. At present, henna (*Lawsonia intermis*) is the most commonly used natural plant dye for hair. However, due to the poor solubility and low concentration of Lawsone, the pigment in henna, a long application time (as much as several hours) is required to produce a weak, dull shade of color. Moreover, Lawsone "has been examined by SCCNFP . . . (and) . . . its latest opinion on Lawsone . . . (is) Lawsone has genotoxicity/mutagenicity potential in vitro and in vivo and that therefore no safe threshold for Lawsone can be established" (SCCNFP/0798/04, 2004).

Furthermore, natural plant dyes generally lack the color fastness and light fastness of synthetic hair color formulations. Problems with the substantivity of plant-based dyes, which is the affinity that a dye has for a particular fiber, have existed for centuries. Mordanting has long been used as a way to increase substantivity of plant dyes. The mordant's function is to form a complex between a polyvalent metal salt and a dye. The application of a mordant traditionally requires at least two steps, and often includes a pre- or post treatment as well. That is because the reaction between mordants and dyes is virtually instantaneous, making it necessary to apply them separately.

The use of mordants has been limited in recent years, however, because of their generally high toxicity. The most common mordants still in use, although rarely, are chromium salts used in the leather industry. Other mordants include salts of aluminum and copper (Joseph Rivlin, The Dyeing of Textile Fibers, PCT&S, Philadelphia, 1992, p. 30-52; H. S. Freeman & A. T. Peters, Colorants for Non-Textile Applications, Elsevier, 2000, pp. 439-448). There are, however, a number of mineral or metal salts that are capable of acting as a mordant, yet lack the toxicity of chromium salts or other typical mordants. Those mineral or metal salts include, but are not limited to, iron gluconate, ferrous aspartate, calcium gluconate, calcium aspartate, magnesium gluconate, magnesium aspartate, magnesium citrate, magnesium palmitate, zinc gluconate, zinc aspartate, and manganese gluconate.

There remains a need for a fast-acting, light fast, wash fast, color fast, natural hair dye formulation which avoids the use of potentially harmful ingredients, and in particular provides bright, intense colors without the use of toxic mordanting agents.

SUMMARY OF THE DISCLOSURE

The present disclosure addresses the above-described need by providing a composition for dyeing keratin fibers, comprising approximately 0.1 to 30 percent of at least one substantially pure plant dye obtained using at least one of a solvent or supercritical CO2 extraction process, and approximately 0.01 to 5 percent of active metal in a mineral or metallic salt capable of acting as a mordanting agent.

The dyes discussed herein are extracts from natural plant material, as opposed to synthetic acid dyes. These natural plant dyes generally are either oil-soluble or have a pH above 4.5. It will be appreciated that the natural plant dyes with a pH above 4.5 or which are oil soluble are further distinguished from acid dyes, which generally are water soluble and have a pH below 4.5.

In a composition according to an embodiment of the disclosure, the plant dye can be selected from the group consisting of Brazilwood, Logwood Extract/Hematine, Hematine, Indigo, Quercetin, Madder, alizarine, rubiethyric acid, purpuroxanthin, rubiadin, morindanigrin, munjistin, morindadiol, carotene, crocetin, bixin, canthaxanthin, lycopene, capsanthin, apocarotenal, xanthophyll, curcumin, morin, malclurin, luteolin, apigenin, fukugetin, datiscetin, kaempferol, rhamnocitrin, rhamnethin, zanthorhamnin, Isorhamnetin, Rhamnazin, Rutin, Gossypetin, Butin/Butein, Rottlerin, Chlorophyll A/B, Catechin, Fisetin, Lapachol, Juglone, Alkannin, Alkannan, Deoxysantalin, Atromentin, Awobamin, Carajuirin, Dracorhodin, Berberine, Betanin, Orcein, Xanthone, Naphthalene, Riboflavin, Anthocyanin, Lawsone, emblica extract, alfalfa extract, black tea extract, green tea extract, white tea extract, and red sandalwood.

The mineral or metallic salt capable of acting as a mordanting agent can be selected from the group consisting of iron gluconate, ferrous aspartate, calcium gluconate, calcium aspartate, sodium gluconate, magnesium gluconate, magnesium aspartate, magnesium citrate, magnesium palmitate, zinc gluconate, zinc aspartate, and manganese gluconate. One or both parts of the above described composition may be encapsulated in a water impermeable shell so that the composition may be used as a one-part hair dye system. Solvent extraction can include hydrocarbon extraction, ultrafiltration, and ion exchange separation.

In accordance with an aspect of the disclosure, a two-part hair dye composition comprises an activator portion including an alcohol and a mineral or metallic salt capable of acting as a mordanting agent, and a color portion including an alcohol and a concentrated plant dye. The composition includes approximately 0.1 to 30 percent of the concentrated plant dye, and approximately 0.01 to 5 percent active metal. As noted above, the plant dye is extracted from natural plant material. The mineral or metallic salt is selected from the group consisting of iron gluconate, ferrous aspartate, copper gluconate, calcium gluconate, calcium aspartate, sodium gluconate, magnesium gluconate, magnesium aspartate, magnesium citrate, magnesium palmitate, zinc gluconate, zinc aspartate, and manganese gluconate. In specific embodiments, the mineral or metallic salt may include sodium gluconate in combination with one or more of zinc gluconate, iron gluconate and copper gluconate. In specific embodiments, the color portion including the concentrated plant dye has a pH above 4.5. The activator portion may include lactic acid, glycerin, benzyl alcohol, isopropyl alcohol and xanthan; the color portion may include lactic acid, glycerin, benzyl alcohol, and xanthan. In specific embodiments, the concentrated plant dye includes one or more of Brazilwood, Logwood Extract/Hematine, Hematine, Indigo, Quercetin, and Madder.

In accordance with an additional aspect of the disclosure, a method of manufacturing a composition for dyeing keratin fibers includes a step of producing a concentrated plant dye, and a step of providing a mineral or metallic salt capable of acting as a mordanting agent, so that the composition includes approximately 0.01 to 5 percent active metal. The concentrated plant dye is produced using at least one of a solvent extraction process and a supercritical CO2 extraction process, so that the composition includes approximately 0.1 to 30 percent of the concentrated plant dye.

DETAILED DESCRIPTION

In embodiments of the disclosure (described in more detail below), substantially pure natural plant dyes were obtained by solvent extraction (e.g., hydrocarbon extraction, ultrafiltration, or ion exchange separation) or supercritical CO2 extraction. These substantially pure dyes produced hue, value and chroma results as bright or brighter than those produced by synthetic dyes when applied to keratin fiber (including human hair). This bright color was produced both with and without the use of mordants.

Two-Part Dyeing System

We have produced with substantially pure plant dyes (isolated by solvent or supercritical CO2 extraction) bright colors with light- and wash-fast properties (stable for more than 40 standard shampoo cycles)—comparable or superior to permanent hair dye formulations—by mixing the substantially pure plant dyes with mineral or metallic salts (e.g., sodium gluconate, zinc gluconate, zinc aspartate, calcium gluconate, copper gluconate or iron gluconate among others) in a two-part or two-step system. These mineral or metallic salts are non-toxic salts that function as mordants when mixed with the substantially pure plant dyes isolated as described above. A useful and unexpected result is that bright, light- and wash-fast colors are obtained with natural plant dyes, as opposed to synthetic acid dyes.

In a two part hair color system according to embodiments of the disclosure, one part is referred to as an activator and the other part is a color. The activator and color may also be referred to as a shampoo and conditioner, respectively. The preferred order of application is activator/shampoo followed by color/conditioner, but the parts can be applied in reverse order and still result in some color deposition.

The activator/shampoo part of the two-part system typically contains the mineral or metallic salt (or salts) in an activator base. The color/conditioner part of the two-part system typically contains the bulk of the natural dye in a color base.

In Tables 1A, 1B, . . . 23A, 23B below, concentrations of various components are listed by weight-weight percentage (w/w %).

According to specific embodiments, compositions of the activator base and color base are given below in Tables 1A and 1B, respectively.

TABLE 1A

Activator Base

| | w/w % |
|---|---|
| De-ionized (DI) water | 83.4% |
| Xanthan | 0.5% |
| Glycerin | 5.4% |
| Lactic Acid | 8.9% |
| Benzyl Alcohol | 1.8% |

TABLE 1B

Color Base

| | w/w % |
|---|---|
| Water | 83.7% |
| Xanthan Gum CG-T | 0.7% |
| Glycerin | 5.4% |
| Plantaren 2000 NUP | 3.6% |
| Benzyl Alcohol | 3.9% |
| Lactic Acid | 2.7% |

The present inventors have found that bases formulated as outlined in Tables 1A and 1B provide effective and even color deposition without interfering with the color shades.

The activator/shampoo part of the two-part system includes the mineral or metallic salts in combination with benzyl and isopropyl alcohols in an aqueous solution. In specific embodiments, the metal salts include sodium gluconate in combination with one or more of zinc gluconate, iron gluconate and copper gluconate. In general, the composition as a whole (including both parts of the two-part system) has approximately 0.01-5% (w/w) of active metal in the mineral or metallic salt.

The color/conditioner part of the two-part system, according to specific embodiments, comprises 0.1-30% (w/w) of a substantially pure natural plant dye or combination of dyes, depending on the color desired, isolated by solvent or supercritical $CO_2$ extraction. The present inventors have found that, in contrast to acid dyes, the natural plant dyes generally have a pH above 4.5.

Compositions for activators and colors for various shades, according to specific embodiments, are given in Tables 2A, 2B, ..., 23A, 23B below. It is understood that the balance of each activator or color composition listed is comprised of the activator or color base (Tables 1A, 1B), respectively.

TABLE 2A

Natural Black 1N activator

| | w/w % |
|---|---|
| Erythorbic Acid | 1% |
| Sodium Gluconate | 3-7% |
| Iron Gluconate | 8-15% |
| Benzyl Alcohol | 5% |
| Isopropyl Alcohol | 0.1-30% |
| Lactic Acid | 3% |

TABLE 2B

Natural Black 1N color

| | w/w % |
|---|---|
| Brazilwood | 0.1-10% |
| Logwood Extract/Hematine | 0.1-20% |
| Indigo | 0.1-10% |

TABLE 3A

Natural Dark Brown 3N activator

| | w/w % |
|---|---|
| Erythorbic Acid | 1% |
| Sodium Gluconate | 3-7% |
| Iron Gluconate | 8-15% |
| Benzyl Alcohol | 5% |
| Isopropyl Alcohol | 0.1-30% |
| Lactic Acid | 2-4% |

TABLE 3B

Natural Dark Brown 3N color

| | w/w % |
|---|---|
| Brazilwood | 0.1-10% |
| Logwood Extract/Hematine | 0.1-20% |
| Indigo | 0.1-10% |

TABLE 4A

Natural Medium Brown 4N activator

| | w/w % |
|---|---|
| Erythorbic Acid | 1% |
| Sodium Gluconate | 3-7% |
| Iron Gluconate | 0.1-25% |
| Benzyl Alcohol | 5% |
| Isopropyl Alcohol | 10-20% |
| Lactic Acid | 2-4% |

TABLE 4B

Natural Medium Brown 4N color

| | w/w % |
|---|---|
| Logwood Extract/Hematine | 0.1-20% |
| Brazilwood | 0.1-5% |
| Indigo | 0.1-5% |

TABLE 5A

Natural Light Brown 5N activator

| | w/w % |
|---|---|
| Erythorbic Acid | 1% |
| Sodium Gluconate | 3-7% |
| Iron Gluconate | 0.1-25% |

TABLE 5A-continued

Natural Light Brown
5N activator

| | w/w % |
|---|---|
| Benzyl Alcohol | 5% |
| Isopropyl Alcohol | 10-20% |
| Lactic Acid | 2-4% |

TABLE 5B

Natural Light Brown
5N color

| | w/w % |
|---|---|
| Logwood Extract/Hematine | 0.1-20% |

TABLE 6A

Natural Dark Blonde
6N activator

| | w/w % |
|---|---|
| Isopropyl Alcohol | 15% |
| Sodium Gluconate | 1% |
| Copper Gluconate | 0.1-20% |
| Iron Gluconate | 0.1-20% |
| Erythorbic Acid | 0.03% |
| Benzyl Alcohol | 5% |
| DI water | 13.6% |
| Lactic Acid | 1.1-3% |

TABLE 6B

Natural Dark Blonde
6N color

| | w/w % |
|---|---|
| Logwood Extract/Hematine | 0.1-20% |
| Quercetin | 0.1-5% |
| Isopropyl Alcohol | 0.1-20% |
| Madder | 0.1-20% |

TABLE 7A

Natural Medium Blonde
7N activator

| | w/w % |
|---|---|
| Isopropyl Alcohol | 15.2% |
| Sodium Gluconate | 1.1% |
| Copper Gluconate | 0.1-20% |
| Iron Gluconate | 0.1-20% |
| Erythorbic Acid | 0.03% |
| Benzyl Alcohol | 5% |
| DI water | 13.6% |
| Lactic Acid | 1.1% |

TABLE 7B

Natural Medium Blonde
7N color

| | w/w % |
|---|---|
| Logwood Extract/Hematine | 0.1-20% |
| Quercetin | 0.1-5% |
| Isopropyl Alcohol | 0.1-20% |
| Madder | 0.1-20% |

TABLE 8A

Natural Light Blonde
8N activator

| | w/w % |
|---|---|
| Erythorbic Acid | 1% |
| Sodium Gluconate | 3-7% |
| Iron Gluconate | 0.1-25% |
| Benzyl Alcohol | 5% |
| Isopropyl Alcohol | 10-20% |
| Lactic Acid | 3% |

TABLE 8B

Natural Light Blonde
8N color

| | w/w % |
|---|---|
| Logwood Extract/Hematine | 0.1-20% |
| Quercetin | 0.1-5% |
| Madder | 2-25% |
| Isopropyl Alcohol | 0.1-5% |

TABLE 9A

Natural Dark Golden
Brown 5GD activator

| | w/w % |
|---|---|
| Erythorbic Acid | 1% |
| Sodium Gluconate | 3-7% |
| Iron Gluconate | 0.1-25% |
| Benzyl Alcohol | 5% |
| Isopropyl Alcohol | 10-20% |
| Lactic Acid | 2-4% |

TABLE 9B

Natural Dark Golden
Brown 5GD color

| | w/w % |
|---|---|
| Madder | 5-30% |
| Logwood Extract/Hematine | 0.1-20% |

TABLE 10A

Natural Medium Golden Brown 7GD activator

| | w/w % |
|---|---|
| Erythorbic Acid | 1% |
| Sodium Gluconate | 3-7% |
| Iron Gluconate | 0.1-25% |
| Benzyl Alcohol | 5% |
| Isopropyl Alcohol | 10-20% |
| Lactic Acid | 2-4% |

TABLE 10B

Natural Medium Golden Brown 7GD color

| | w/w % |
|---|---|
| Madder | 0.1-25% |
| Logwood Extract/Hematine | 0.1-10% |

TABLE 11A

Natural Light Golden Brown 9GD activator

| | w/w % |
|---|---|
| Erythorbic Acid | 1% |
| Sodium Gluconate | 3-7% |
| Iron Gluconate | 0.1-25% |
| Benzyl Alcohol | 5% |
| Isopropyl Alcohol | 10-20% |
| Lactic Acid | 2-4% |

TABLE 11B

Natural Light Golden Brown 9GD color

| | w/w % |
|---|---|
| Madder | 0.1-20% |
| Logwood Extract/Hematine | 0.1-5% |
| Quercetin | 0.1-5% |

TABLE 12A

Natural Copper Gold 8CG activator

| | w/w % |
|---|---|
| Erythorbic Acid | 1% |
| Sodium Gluconate | 3-7% |
| Iron Gluconate | 0.1-25% |
| Benzyl Alcohol | 5% |
| Isopropyl Alcohol | 10-20% |
| Lactic Acid | 2-4% |

TABLE 12B

Natural Copper Gold 8CG color

| | w/w % |
|---|---|
| Madder | 0.1-25% |
| Quercetin | 0.1-5% |
| IPA Slurry | 0.1-10% |

TABLE 13A

Natural Dark Bright Copper 6BC activator

| | w/w % |
|---|---|
| DI water | 14% |
| Sodium Gluconate | 0.1-3% |
| Zinc Gluconate | 0.1-20% |
| Benzyl Alcohol | 5% |
| Isopropyl Alcohol | 10-20% |

TABLE 13B

Natural Dark Bright Copper 6BC color

| | w/w % |
|---|---|
| Madder 1802 | 0.1-30% |

TABLE 14A

Natural Medium Bright Copper 7BC activator

| | w/w % |
|---|---|
| DI water | 14% |
| Sodium Gluconate | 0.1-3% |
| Zinc Gluconate | 0.1-20% |
| Benzyl Alcohol | 5% |
| Isopropyl Alcohol | 10-20% |

TABLE 14B

Natural Medium Bright Copper 7BC color

| | w/w % |
|---|---|
| Madder | 0.1-30% |

TABLE 15A

Natural Medium Bright Copper 8BC activator

| | w/w % |
|---|---|
| DI water | 14% |
| Sodium Gluconate | 0.1-3% |
| Zinc Gluconate | 0.1-20% |
| Benzyl Alcohol | 5% |
| Isopropyl Alcohol | 10-20% |

TABLE 15B

Natural Medium Bright Copper 8BC color

| | w/w % |
|---|---|
| Madder | 0.1-25% |

TABLE 16A

Natural Medium Red Copper 6CR activator

| | w/w % |
|---|---|
| DI Water | 11.2% |
| Sodium Gluconate | 0.1-3% |
| Zinc Gluconate | 0.1-20% |
| Copper Gluconate | 0.1-20% |
| Lactic Acid | 1.4% |
| Isopropyl Alcohol | 10-20% |
| Erythorbic Acid | 0.2% |
| Benzyl Alcohol | 5% |

TABLE 16B

Natural Medium Red Copper 6CR color

| | w/w % |
|---|---|
| Madder | 0-25% |
| Brazilwood | 0.1-10% |

TABLE 17A

Natural Light Red Copper 7CR activator

| | w/w % |
|---|---|
| DI water | 14% |
| Sodium Gluconate | 0.1-10% |
| Zinc Gluconate | 0.1-20% |
| Benzyl Alcohol | 5% |
| Isopropyl Alcohol | 10-20% |

TABLE 17B

Natural Light Red Copper 7CR color

| | w/w % |
|---|---|
| Brazilwood | 0.1-20% |
| Hematine | 0.1-20% |
| Quercetin | 0.1-10% |

TABLE 18A

Natural Fiery Red Brown 4FR activator

| | w/w % |
|---|---|
| Isopropyl Alcohol | 10-20% |
| Sodium Gluconate | 0.1-10% |
| Copper Gluconate | 0.1-20% |

TABLE 18A-continued

Natural Fiery Red Brown 4FR activator

| | w/w % |
|---|---|
| Benzyl Alcohol | 5% |
| DI water | 13% |
| Lactic Acid | 1% |

TABLE 18B

Natural Fiery Red Brown 4FR color

| | w/w % |
|---|---|
| Brazilwood | 0.1-20% |
| Hematine | 0.1-20% |
| Quercetin | 0.1-10% |

TABLE 19A

Natural Fiery Red Light Brown 5FR activator

| | w/w % |
|---|---|
| Isopropyl Alcohol | 10-20% |
| Sodium Gluconate | 0.1-10% |
| Copper Gluconate | 0.1-20% |
| Benzyl Alcohol | 5% |
| DI water | 13% |
| Lactic Acid | 1% |

TABLE 19B

Natural Fiery Red Light Brown 5FR color

| | w/w % |
|---|---|
| Brazilwood | 0.1-30% |
| Hematine | 5% |
| IPA | 5-15% |

TABLE 20A

Natural Light Mahogany Brown 5MH activator

| | w/w % |
|---|---|
| Isopropyl Alcohol | 10-20% |
| Sodium Gluconate | 0.1-10% |
| Copper Gluconate | 0.1-20% |
| Benzyl Alcohol | 5% |
| DI water | 13% |
| Lactic Acid | 1% |

TABLE 20B

Natural Light Mahogany Brown 5MH color

| | w/w % |
|---|---|
| Brazilwood | 0.1-20% |
| Hematine | 0.1-20% |
| IPA | 5-15% |

TABLE 21A

Natural Very Light Mahogany
Brown 6MH activator

|  | w/w % |
| --- | --- |
| Isopropyl Alcohol | 10-20% |
| Sodium Gluconate | 0.1-10% |
| Copper Gluconate | 0.1-20% |
| Benzyl Alcohol | 5% |
| DI water | 13% |
| Lactic Acid | 1% |

TABLE 21B

Natural Very Light
Mahogany Brown 6MH color

|  | w/w % |
| --- | --- |
| Brazilwood | 0.1-15% |
| Hematine | 0.1-15% |

TABLE 22A

Natural Medium Ash
Blonde 7AH activator

|  | w/w % |
| --- | --- |
| Erythorbic Acid | 1% |
| Sodium Gluconate | 3-7% |
| Iron Gluconate | 0.1-25% |
| Benzyl Alcohol | 5% |
| Isopropyl Alcohol | 10-20% |
| Lactic Acid | 2-4% |

TABLE 22B

Natural Medium Ash
Blonde 7AH color

|  | w/w % |
| --- | --- |
| Madder | 0.1-15% |
| Hematine | 0.1-20% |
| Brazilwood | 0.1-10% |

TABLE 23A

Natural Mocha Brown
4MO activator

|  | w/w % |
| --- | --- |
| Isopropyl Alcohol | 10-20% |
| Sodium Gluconate | 0.1-15% |
| Copper Gluconate | 0.1-15% |
| Benzyl Alcohol | 5% |
| DI water | 7% |
| Lactic Acid | 1-3% |
| Erythorbic Acid | 0.5% |
| Iron Gluconate | 0.1-15% |

TABLE 23B

Natural Mocha Brown
4MO color

|  | w/w % |
| --- | --- |
| Quercetin | 0.1-10% |
| Hematine | 0.1-15% |
| Brazilwood | 0.1-15% |

The activator part and the color part of the two-part system in these embodiments contain acids (specifically, lactic acid in the activator base and the color base, and lactic and erythorbic acids in several of the specific activators listed above). The present inventors have found, however, that effective hair coloring using natural plant dyes and mineral/metallic salts in accordance with the present disclosure is not dependent on the pH of the dye. Accordingly, acids may optionally be omitted from the hair dye system. Lactic acid is specifically included in the above-listed formulations to inhibit unwanted microbial growth. In additional embodiments, lactic acid is omitted from the formulations listed above; another suitable anti-microbial agent may be used.

In a typical application of a two-part hair dye according to the disclosure, the activator/shampoo part of the two-part hair color system is rubbed into the hair and allowed to sit for 1-10 minutes, at which point the color/conditioner part of the two-part system is added to the hair, rubbed in, and allowed to sit for approximately 20 minutes. The total time is dependent on the color required. For example, if the color being applied was a shade of brown, the longer the solution is left on the hair the darker the shade of brown that will result.

One-Part Dyeing System with Encapsulation

Another useful and unexpected result was obtained when either the substantially pure plant dye and/or the mineral or metallic salt was encapsulated in a lipid, gelatin, calcium alginate, polymethyl methacrylate urea (PMMU), or other water impermeable shell. The encapsulation of either the plant dye, the mineral or metallic salt, or both allows the dye and salt to be combined together into an aqueous solution that can be used in formulations including but not limited to color gels, color creams, color shampoos, color conditioners, and the like. This compatibility is not possible absent the encapsulation step because of the speed with which the mordant reacts with the dye to form an insoluble complex that precipitates out of solution, and is less effective as a dye due to the insoluble complex of mordant and dye forming outside of the presence of keratin fiber. Moreover, these formulations with an encapsulated part are stable for long periods of time (more than 6 months), yet can be applied as a one-step, quick-action hair color (i.e., a one-part system) to color human hair in 10-20 minutes or less.

In another embodiment, the one-part system described just above comprises the same components, in the same percentages, as the composition for the two-part system described earlier. However, in the one-part system, the zinc salt is encapsulated in a shell of hydrogenated castor oil and/or crosslinked with coacervated gelatin, calcium alginate, or PMMU. Such a coating can be applied by spray drying, fluid bed drying, or any other method known in the art.

Another useful and unexpected result is that the color produced is leveled without the addition of a leveling agent. It will be appreciated that it is often desirable to promote sustained release of either the mineral supplement, the dye, or both after the core amount of both dye and supplement are released. This may be done by providing a gradient of concentrations of both metal action and dye to conduct kinetics on the process as in regular dyeing systems based on specially synthesized dyes, using techniques known in the art.

By overcoming the problem of compatibility inherent in combining substantially pure plant dyes and mineral or metal salts (acting as a mordant) through the use of encapsulation, natural plant dyes can be used in a one-part system for applications such as:

(1) 100% plant-based permanent hair color.

(2) 100% plant-based semi-permanent hair color.

(3) 100% plant-based demi-permanent hair color (4) 100% plant-based liquid color gel.

(5) 100% plant-based color shampoo (6) 100% plant-based color conditioner.

(7) 100% plant-based hair color and fixative all in one (8) 100% plant-based hair color and bleach all in one (9) Any other hair color formulation implying use of natural plant based dye.

Application

The application of all these formulations is very similar to the application of hair color systems employing conventional synthetic dyes (including acid dyes), but without the potential risks of toxicity, irritation and hair damage inherent in those dye systems.

By combining the technologies of substantially pure plant dyes obtained by solvent or supercritical CO2 extraction, and mordanting with mineral or metallic salts in combination with or without encapsulation, we have been able to create safe hair dyes that unexpectedly and surprisingly produce bright and permanent or semi-permanent colors similar to synthetic dyes in 10-20 minutes or less, thereby improving on the safety, durability, quality and application time of existing products on the market.

The natural hair dyes described herein are not limited only to the embodiments described. It is contemplated that such embodiments will include not only those described above but also embodiments comprising any number of other ingredients necessary for hair dye products such as those described. Such ingredients would include anionic surfactants, cationic surfactants, nonionic surfactants and amphoteric surfactants, as well as anionic emulsifiers, cationic emulsifiers, nonionic emulsifiers and amphoteric emulsifiers and any other ingredients necessary to practice the invention, including but not limited to solvents, fragrances, thickeners, humectants, polymers, plasticizers, conditioners, and preservatives. Numerous other alternatives, modifications and variations will be apparent to those skilled in the art. Accordingly, the invention is intended to encompass all such other embodiments, alternatives, modifications and variations which fall within the scope and spirit of the disclosure and the following claims.

We claim:

1. A composition for dyeing keratin fibers, comprising:
   approximately 0.1 to 30 percent of at least one concentrated plant dye; and
   a mineral or metallic salt with approximately 0.01 to 5 percent active metal capable of acting as a mordanting agent,
   wherein the mineral or metallic salt is selected from the group consisting of iron gluconate, ferrous aspartate, copper gluconate, calcium gluconate, calcium aspartate, sodium gluconate, magnesium gluconate, magnesium aspartate, magnesium citrate, magnesium palmitate, zinc gluconate, zinc aspartate, and manganese gluconate.

2. The composition according to claim 1, wherein the concentrated plant dye has a pH above 4.5.

3. The composition according to claim 1, wherein the mineral or metallic salt includes one or more of sodium gluconate, zinc gluconate, iron gluconate and copper gluconate.

4. The composition according to claim 1, wherein the concentrated plant dye is an extract from natural plant material, and is either oil soluble or has a pH above 4.5.

5. The composition according to claim 4, wherein the concentrated plant dye is extracted using at least one of a solvent extraction process and a supercritical CO2 extraction process.

6. The composition according to claim 1, wherein said composition is a two-part hair dye system.

7. The composition according to claim 1, wherein the at least one concentrated plant dye is selected from the group consisting of Brazilwood, Logwood Extract/Hematine, Hematine, Indigo, Quercetin, Madder, alizarine, rubiethyric acid, purpuroxanthin, rubiadin, morindanigrin, munjistin, morindadiol, carotene, crocetin, bixin, canthaxanthin, lycopene, capsanthin, apocarotenal, xanthophyll, curcumin, morin, malclurin, luteolin, apigenin, fukugetin, datiscetin, kaempferol, rhamnocitrin, rhamnethin, zanthorhamnin, Isorhamnetin, Rhamnazin, Rutin, Gossypetin, Butin/Butein, Rottlerin, Chlorophyll A/B, Catechin, Fisetin, Lapachol, Juglone, Alkannin, Alkannan, Deoxysantalin, Atromentin, Awobamin, Carajuirin, Dracorhodin, Berberine, Betanin, Orcein, Xanthone, Naphthalene, Riboflavin, Anthocyanin, Lawsone, emblica extract, alfalfa extract, black tea extract, green tea extract, white tea extract, and red sandalwood.

8. The composition according to claim 5, wherein the concentrated plant dye is extracted using a solvent extraction process.

9. The composition according to claim 8, wherein the solvent extraction process is selected from the group consisting of hydrocarbon extraction, ultrafiltration, and ion exchange separation.

10. The composition according to claim 5, further comprising a surfactant selected from the group consisting of anionic surfactants, cationic surfactants, nonionic surfactants and amphoteric surfactants.

11. The composition according to claim 5, further comprising an emulsifier selected from the group consisting of anionic emulsifiers, cationic emulsifiers, nonionic emulsifiers and amphoteric emulsifiers.

12. A two-part hair dye composition, comprising:
    an activator portion including an alcohol and a mineral or metallic salt capable of acting as a mordanting agent; and
    a color portion including an alcohol and a concentrated plant dye,
    wherein
        the composition includes approximately 0.1 to 30 percent of the concentrated plant dye,
        the composition includes approximately 0.01 to 5 percent active metal, and
        the mineral or metallic salt is selected from the group consisting of iron gluconate, ferrous aspartate, copper gluconate, calcium gluconate, calcium aspartate, sodium gluconate, magnesium gluconate, magnesium aspartate, magnesium citrate, magnesium palmitate, zinc gluconate, zinc aspartate, and manganese gluconate.

13. The two-part hair dye composition according to claim 12, wherein the mineral or metallic salt includes sodium gluconate in combination with one or more of zinc gluconate, iron gluconate and copper gluconate.

14. The two-part hair dye composition according to claim 12, wherein the color portion has a pH above 4.5.

15. The composition according to claim 12, wherein the concentrated plant dye is an extract from natural plant material, and is either oil soluble or has a pH above 4.5.

16. The two-part hair dye composition according to claim 12, wherein
the activator portion further comprises lactic acid, glycerin, benzyl alcohol, isopropyl alcohol and xanthan; and
the color portion further comprises lactic acid, glycerin, benzyl alcohol, and xanthan.

17. The two-part hair dye composition according to claim 12, wherein
the activator portion further comprises glycerin, benzyl alcohol, isopropyl alcohol and xanthan; and
the color portion further comprises glycerin, benzyl alcohol, and xanthan.

18. The two-part hair dye composition according to claim 12, wherein the composition is substantially free of acid.

19. The two-part hair dye composition according to claim 12, wherein the concentrated plant dye includes one or more of Brazilwood, Logwood Extract/Hematine, Hematine, Indigo, Quercetin, and Madder.

20. A method of manufacturing a composition for dyeing keratin fibers, comprising the steps of:
producing a concentrated plant dye using at least one of a solvent extraction process and a supercritical CO2 extraction process, so that the composition includes approximately 0.1 to 30 percent of the concentrated plant dye; and
providing a mineral or metallic salt capable of acting as a mordanting agent, so that the composition includes approximately 0.01 to 5 percent active metal,
wherein
the mineral or metallic salt is selected from the group consisting of iron gluconate, ferrous aspartate, copper gluconate, calcium gluconate, calcium aspartate, sodium gluconate, magnesium gluconate, magnesium aspartate, magnesium citrate, magnesium palmitate, zinc gluconate, zinc aspartate, and manganese gluconate.

21. The method according to claim 20, wherein the concentrated plant dye has a pH above 4.5.

22. The method according to claim 20, wherein the mineral or metallic salt includes one or more of sodium gluconate, zinc gluconate, iron gluconate and copper gluconate.

23. The method according to claim 20, wherein said composition is a two-part hair dye system.

24. The method according to claim 20, wherein the concentrated plant dye is selected from the group consisting of Brazilwood, Logwood Extract/Hematine, Hematine, Indigo, Quercetin, Madder, alizarine, rubiethyric acid, purpuroxanthin, rubiadin, morindanigrin, munjistin, morindadiol, carotene, crocetin, bixin, canthaxanthin, lycopene, capsanthin, apocarotenal, xanthophyll, curcumin, morin, malclurin, luteolin, apigenin, fukugetin, datiscetin, kaempferol, rhamnocitrin, rhamnethin, zanthorhamnin, Isorhamnetin, Rhamnazin, Rutin, Gossypetin, Butin/Butein, Rottlerin, Chlorophyll A/B, Catechin, Fisetin, Lapachol, Juglone, Alkannin, Alkannan, Deoxysantalin, Atromentin, Awobamin, Carajuirin, Dracorhodin, Berberine, Betanin, Orcein, Xanthone, Naphthalene, Riboflavin, Anthocyanin, Lawsone, emblica extract, alfalfa extract, black tea extract, green tea extract, white tea extract, and red sandalwood.

* * * * *